United States Patent [19]
Goffe

[11] Patent Number: 5,882,918
[45] Date of Patent: Mar. 16, 1999

[54] CELL CULTURE INCUBATOR

[75] Inventor: Randal A. Goffe, Arlington, Wash.

[73] Assignee: Genespan Corporation, Redmond, Wash.

[21] Appl. No.: 740,729

[22] Filed: Nov. 1, 1996

Related U.S. Application Data

[63] Continuation-in-part of Ser. No. 512,546, Aug. 8, 1995, Pat. No. 5,622,857, which is a continuation-in-part of PCT/US94/02140, Feb. 9, 1994..

[51] Int. Cl.$^6$ .................................................. C12M 1/38
[52] U.S. Cl. ..................................... 435/286.6; 435/297.4; 435/298.2; 435/303.3; 435/809
[58] Field of Search .............................. 435/286.1, 286.5, 435/286.6, 286.7, 289.1, 297.2, 297.4, 298.2, 303.1, 303.3, 809; 219/399, 400

[56] References Cited

U.S. PATENT DOCUMENTS

| | | | |
|---|---|---|---|
| 4,033,825 | 7/1977 | Haddad et al. | 435/809 |
| 4,250,266 | 2/1981 | Wade | 435/303.1 |
| 4,391,912 | 7/1983 | Yoshida et al. | 435/297.4 |
| 4,720,462 | 1/1988 | Rosenson | 435/297.4 |
| 4,868,122 | 9/1989 | Kominek et al. | 435/303.1 |
| 5,360,741 | 11/1994 | Hunnell | 435/303.1 |
| 5,424,209 | 6/1995 | Kearney | 435/297.4 |
| 5,455,175 | 10/1995 | Wittwer et al. | 435/286.6 |
| 5,622,857 | 4/1997 | Goffe | 435/297.4 |

FOREIGN PATENT DOCUMENTS

| | | | |
|---|---|---|---|
| 0 293 782 | 12/1988 | European Pat. Off. | 435/303.1 |
| 0339824 | 2/1989 | European Pat. Off. | |
| 0 343 357 | 11/1989 | European Pat. Off. | 435/297.4 |
| 0 419 234 | 3/1991 | European Pat. Off. | 435/297.4 |
| 2588565 | 4/1987 | France . | |
| 62-77524 | 4/1987 | Japan | 435/286.1 |

*Primary Examiner*—William H. Beisner
*Attorney, Agent, or Firm*—Christensen O'Connor Johnson & Kindness PLLC

[57] ABSTRACT

A cell culture incubator has a chamber divided into an incubation portion and a control portion. The incubation portion is adapted to contain a cell culture receptacle. A cell culture receptacle agitator is located in the control portion of the incubator and linkage between the cell culture receptacle agitator and the incubation portion of the chamber causes agitation of the cell culture receptacle. A heater in the control portion of the chamber heats air from the external environment and transports the heated air to the incubation portion of the chamber. A wall divides the chamber into the incubation portion and the control portion. The heater may be a forced air heater that provides a positive pressure to the incubation portion of the chamber to reduce contamination in the incubation portion. A nutrient and gas circulation system communicates with the cell culture receptacle in the incubation portion of the chamber. The nutrient and gas circulation system includes a gas source external to the incubation portion of the chamber and tubing provides communication between the gas source, the cell culture receptacle in the incubation portion of the chamber, and nutrient media. A filter in an opening of the incubation portion of the chamber communicates with the tubing to remove contaminants from gas emanating from the cell culture receptacle prior to venting to the external environment.

12 Claims, 11 Drawing Sheets

CELL CULTURE INCUBATOR

STATEMENT OF RELATED APPLICATIONS

This application is a continuation in part of U.S. Pat. No. 5,622,857 filed Aug. 8, 1995, as application Ser. No. 08/512,546, which is in turn a continuation in part of PCT/US94/02140 filed Feb. 9, 1994.

FIELD OF THE INVENTION

This invention relates to an incubator instrument for the operation of perfusion cell culture processes on the laboratory bench without any special sterility or biohazard features in the working environment. In addition, this invention provides the means for mixing both perfusion and non-perfusion based cell culture processes. Furthermore, the means for achieving a controlled $CO_2$ atmosphere and the required temperature (e.g., at 37° C.) is provided for perfusion, mixed and static cultures. Additionally, the invention relates to the use of poly anionic media additives which enhance attachment of adherent cells to microcarriers while mixing at relatively high speeds, and provide other benefits by facilitating in vivo-like conditions in perfusion culture systems.

BACKGROUND OF THE INVENTION

The standard practice in cell culture is to employ a $CO_2$ incubator to provide the gaseous atmosphere and temperature control required in static culture processes. These processes include the use of multiwell plates, culture dishes, flasks and the like. The relatively large size of standard $CO_2$ incubators (with an inside working volume of about 19 in. wide×26 in. high×19 in. deep), has been used to accommodate small scale processes employing perfusion and mixing equipment, such as pumps and roller mills. Besides being highly inconvenient, such use of $CO_2$ incubators require substantial capital expenditures and space utilization.

From a process efficiency standpoint, perfuision cell culture processes in which $O_2/CO_2$ containing gases are provided to the cultured cells by a direct means are the methods of choice. Various costly, cumbersome, and complex instrument systems have been developed to operate perfusion and mix/stirred culture systems. While performance improvements can be achieved with such systems, they are invariably dedicated and rather inflexible instruments. Also, the failure rate of these stand alone instruments tend to be relatively high. The primary cause of failure is a malfunction of the hot plate which is typically employed for heating the media reservoir. Reports from users of the heater overshooting the set point and an inability to accurately control the temperature in long-term experiments are not uncommon. Most important of all, the instruments are extremely user unfriendly; often requiring years of experience in order to competently conduct a series of complete procedures without the intervention of a technical expert.

The creation of in vivo-like conditions in cell culture systems is a long-standing challenge. Perfusion and mixed/stirred systems are particularly problematic because cells are exposed to shear forces and other effects related to motion which are not normally experienced in vivo. While attachment factors and extracellular matrix components have become increasing employed in the last 20 years, they remain a research curiosity primarily due to economic reasons. An inexpensive cell culture media additive is required which has general applicability. Such a molecule should fulfill the following three requirements:

(i) enhance cell adhesion in a non-selective way, such that mixing/stirring can proceed efficiently in large scale culture systems;

(ii) manipulations of cells in culture (e.g., genetic transformations) must proceed unimpeded; and, (iii) culture conditions approaching the cellular environment found in tissues must be advanced.

Definitions $CO_2$—carbon dioxide gas for maintaining pH, in combination with bicarbonate buffer in the cell culture nutrient media.

Incubator—an instrument designed to provide the culture environment for cells.

$O_2$—oxygen gas, necessary for biological cells to respire.

HPBr—high performance (hollow fiber) bioreactor; a perfusion cell culture device having, for example, a central bi-directional hollow fiber bundle that supplies media, and an outer fiber bundle area that supplies oxygen needed for cell culture.

cpm—cycles per minute, which is the number of 120 degree (for example) complete bi-directional partial rotations of the device in the period of a minute.

Lipofection—introduction of foreign DNA into a host cell which is mediated by cationic lipids that form positively charged liposomes.

Transfection—a process whereby foreign DNA, which is not capable of integrating into the host cell's genome, is introduced into the host cell.

SUMMARY OF THE INVENTION

A cell culture incubator has a chamber divided into an incubation portion and a control portion. The incubation portion is adapted to contain a cell culture receptacle. A cell culture receptacle agitator is located in the control portion of the incubator and linkage between the cell culture receptacle agitator and the incubation portion of the chamber causes agitation of the cell culture receptacle. A heater in the control portion of the chamber heats air from the external environment and transports the heated air to the incubation portion of the chamber. A wall divides the chamber into the incubation portion and the control portion. The heater may be a forced air heater that provides a positive pressure to the incubation portion of the chamber to reduce contamination in the incubation portion. A nutrient and gas circulation system communicates with the cell culture receptacle in the incubation portion of the chamber. The nutrient and gas circulation system includes a gas source external to the incubation portion of the chamber and tubing provides communication between the gas source, the cell culture receptacle in the incubation portion of the chamber, and nutrient media. A filter in an opening of the incubation portion of the chamber communicates with the tubing to remove contaminants from gas emanating from the cell culture receptacle prior to venting to the external environment.

The invention provides a small footprint benchtop incubator instrument designed to accommodate perfusion mixed and static cell culture processes. To accommodate perfusion processes, the invention is equipped with a peristaltic pump for use with sterile disposable tubing sets of varying configurations. The tubing sets provide the means for circulate nutrient media from a reservoir. $O_2/CO_2$ containing gases are supplied from a premixed gas cylinder, and sterility/biohazard concerns are addressed by a series of strategically placed 0.22 μm hydrophobic disc filters. The tubing set design enables a closed loop recirculation of gases and, optionally, an auxiliary supply of the defined gas mixture can be delivered to a disposable flow through chamber which can contain culture plates, flasks and the like. Alternatively, the gas flow tubing set can be modified to supply sterile defined $O_2/CO_2$ gas mixtures to roller bottle cultures and the like. Temperature is maintained in the working volume of the incubator by thermostatically controlled recirculating air, which is maintained at positive pressure relative to ambient conditions. The invention further provides a means for mixing either a perfusion or other batch culture vessels, such as a culture flask or bottle. Sufficient space is provided in the working volume of the incubator such that a reasonable number of culture dishes or flasks can be cultured under identical conditions, which may be critical in process development and scale-up activities. Thus, controls or even inoculum expansion can be cultured in parallel.

In addition, the invention provides for the use of chondroitin sulfate (type C) as a cell culture media additive to enhance adhesion of anchorage dependent cells to microcarriers while mixing and stirring.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENTS

Figure 1:
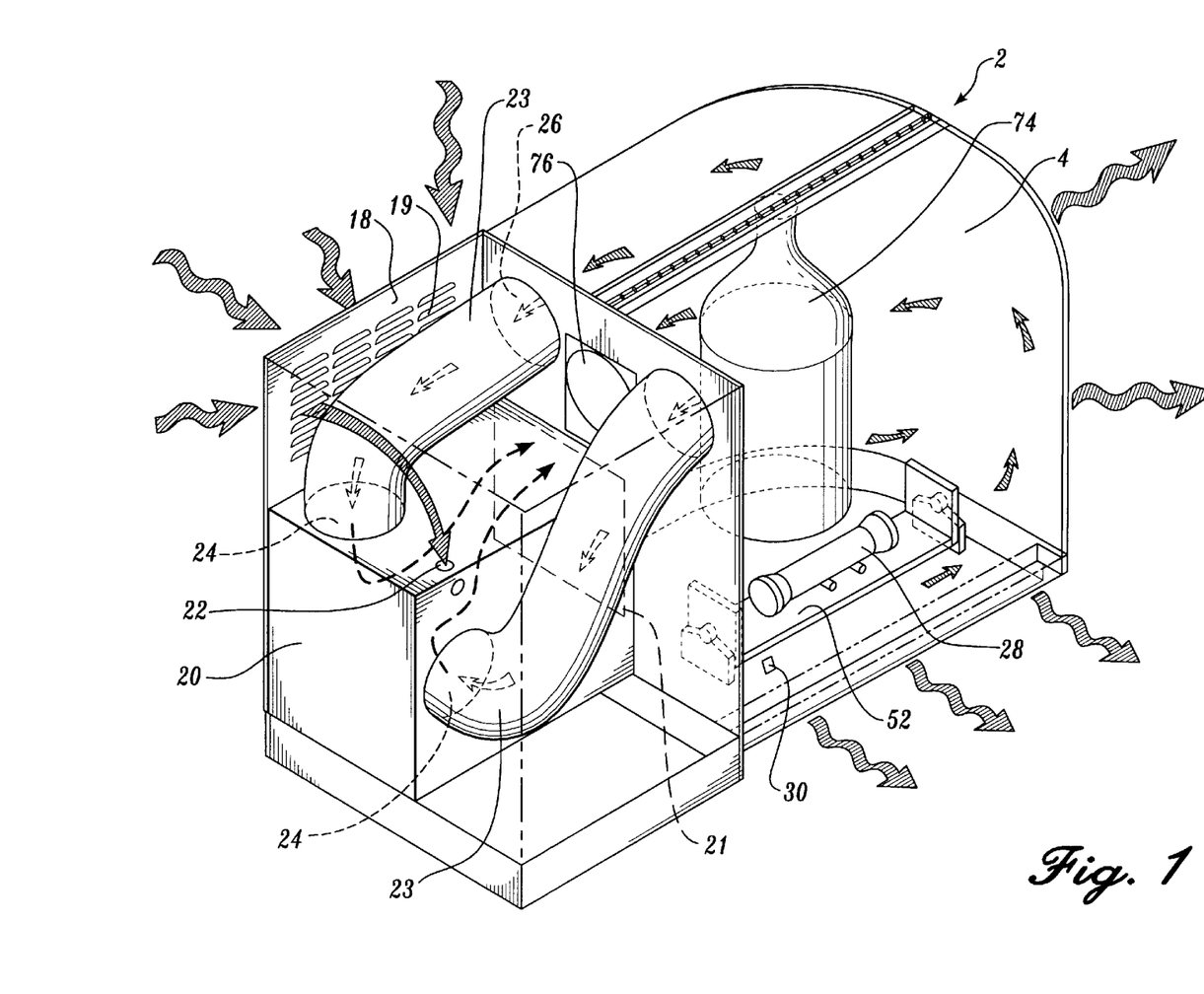
FIG. 1 is a perspective view, partially exposed, showing the cell culture incubator of the present invention.
Figure 2:
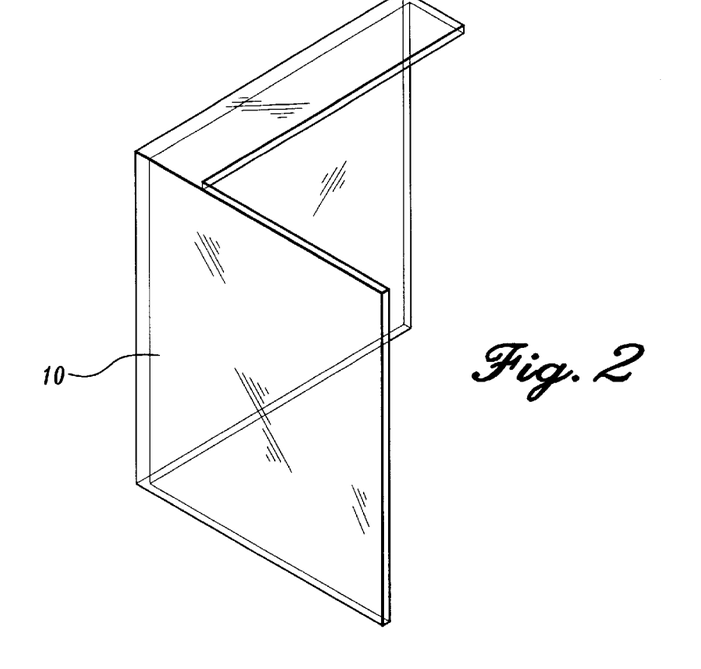
FIG. 2 is a perspective view of a first modular component of the chamber of the cell culture incubator of the present invention.
Figure 3:
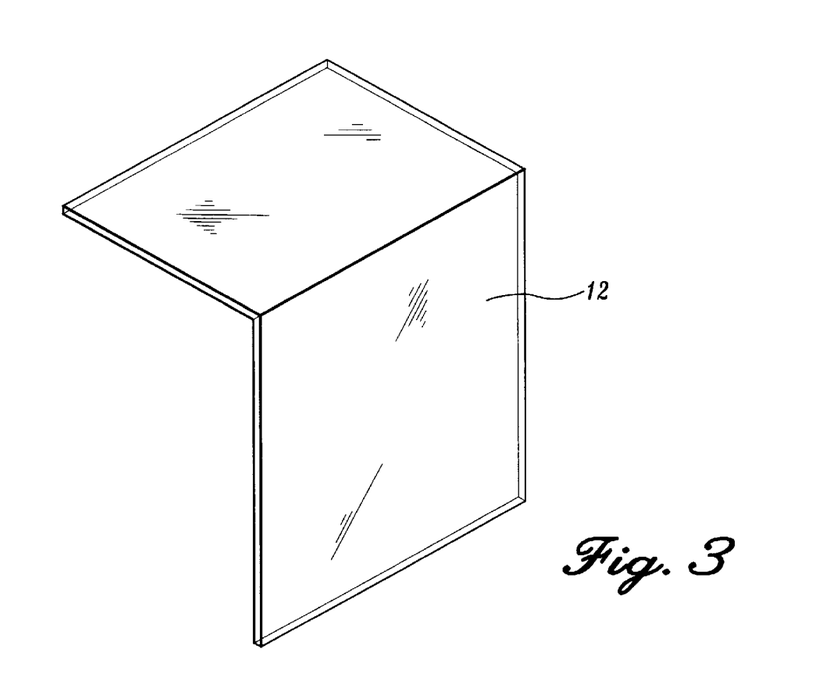
FIG. 3 is a perspective view of a second modular component of the chamber of the cell culture incubator of the present invention.
Figure 4:
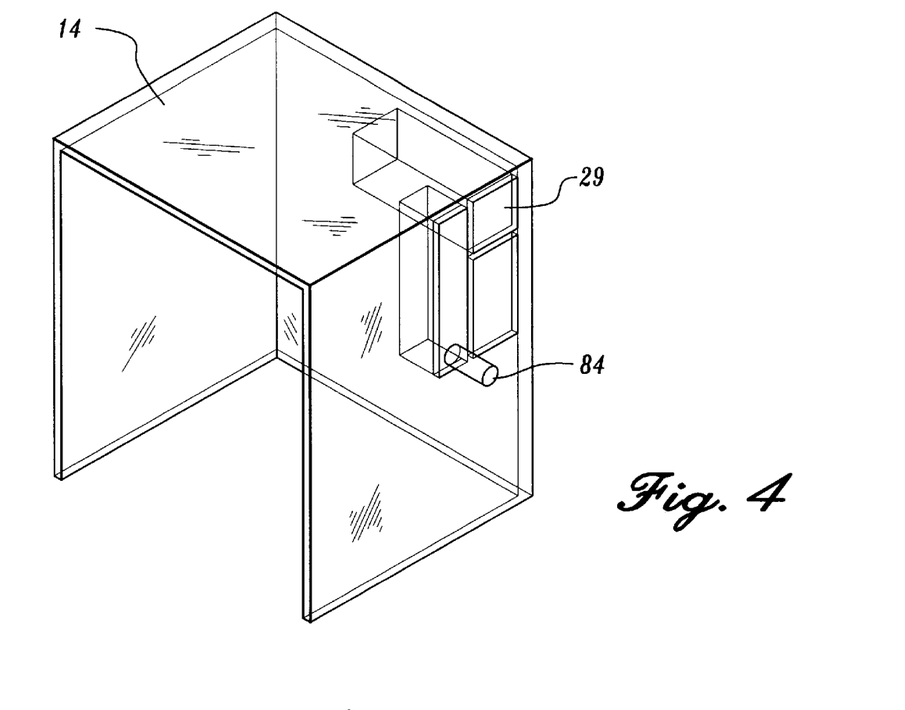
FIG. 4 is a perspective view of a third modular component of the chamber of the cell culture incubator of the present invention.
Figure 5:
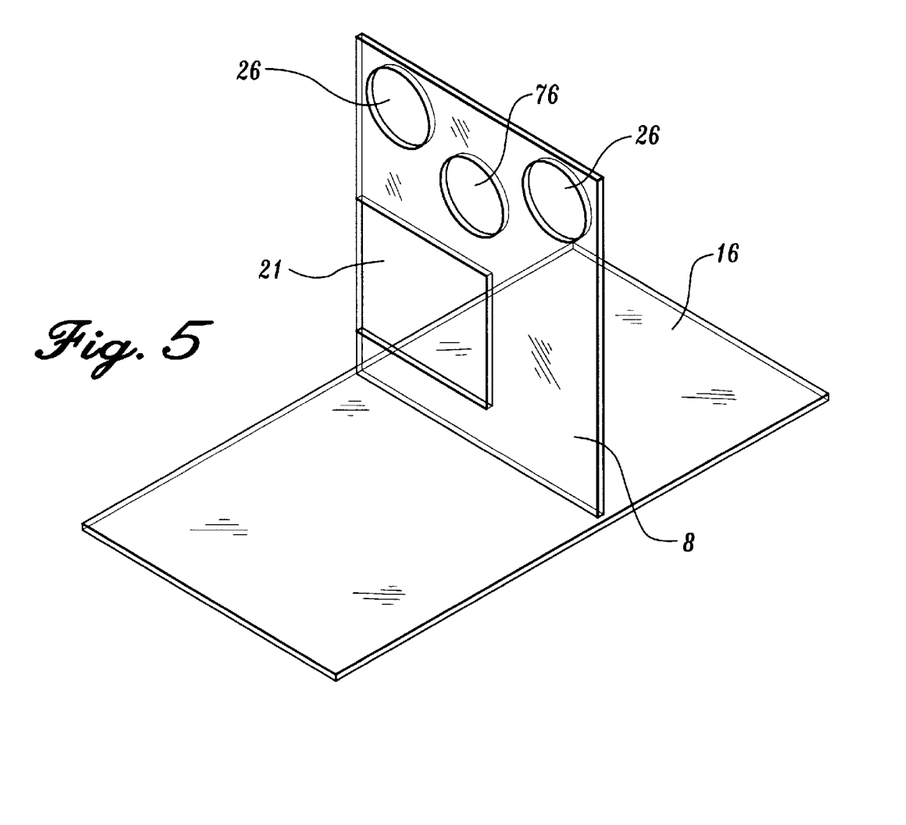
FIG. 5 is a perspective view of a fourth modular component of the chamber of the cell culture incubator of the present invention.
Figure 6:
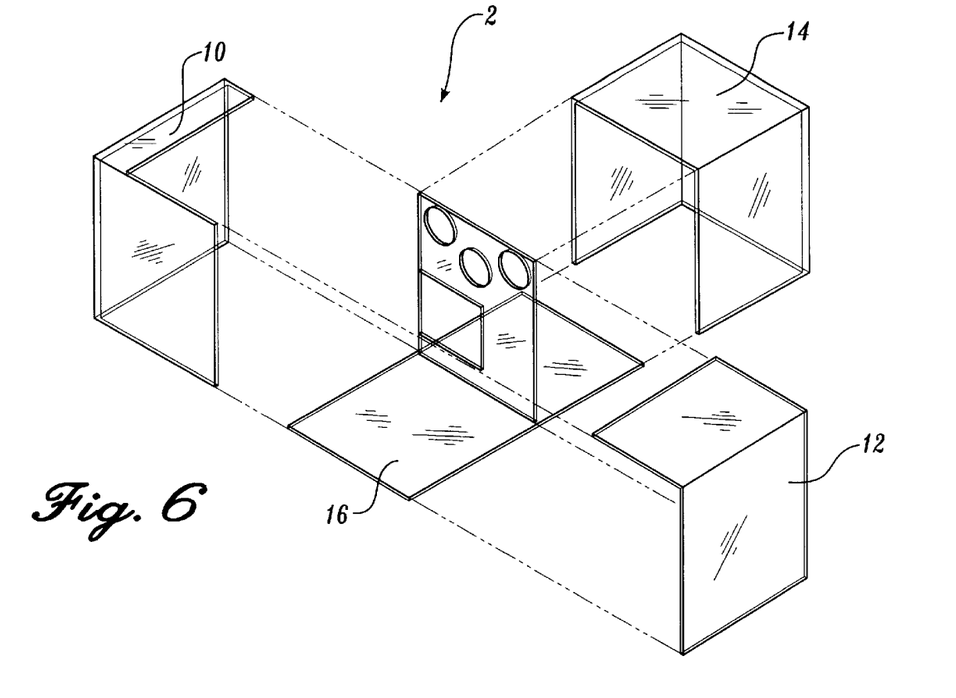
FIG. 6 is an exploded perspective view of the interrelationship between the four components of FIGS. 2 through 5 that form the chamber of the cell culture incubator of the present invention.
Figure 7:
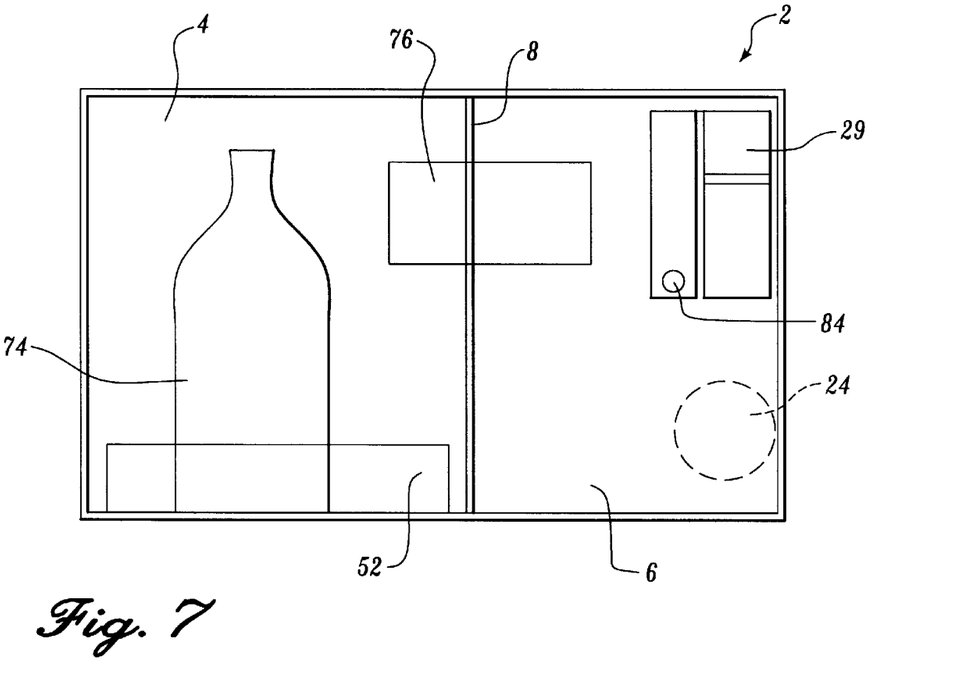
FIG. 7 is an exposed front view of the cell culture incubator of the present invention.
Figure 8:
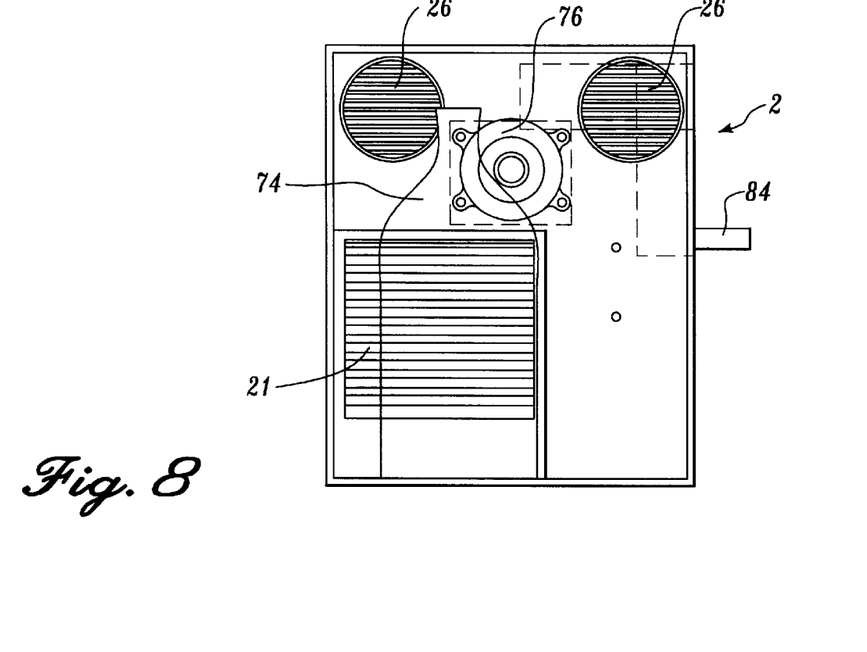
FIG. 8 is an exposed end view of the cell culture incubator of the present invention.
Figure 9:
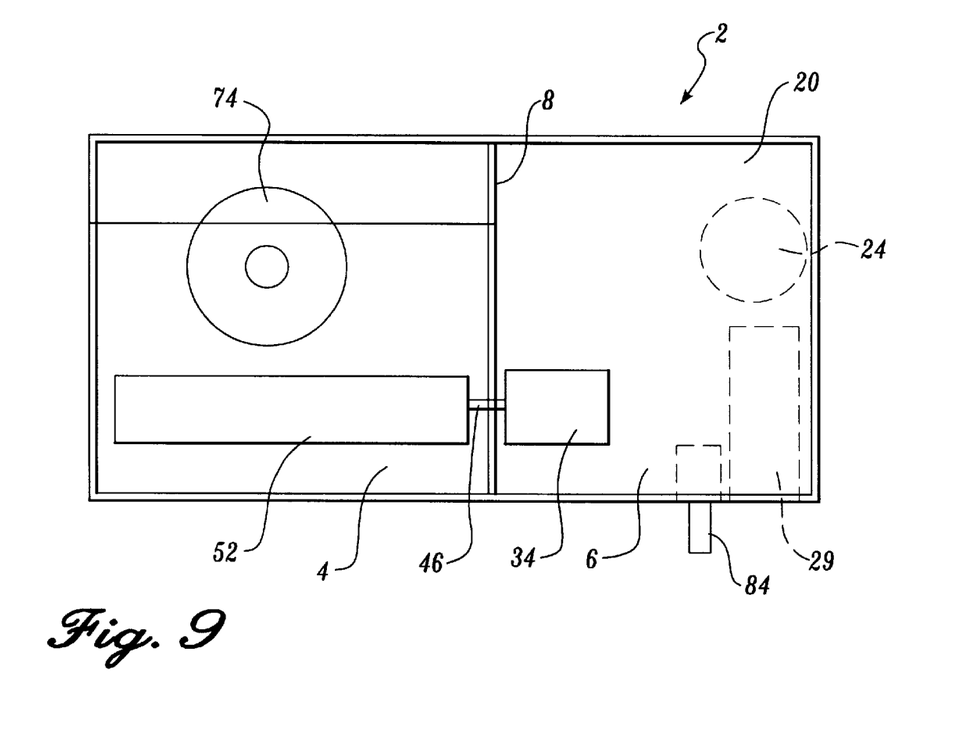
FIG. 9 is an exposed view of the cell culture incubator of the present invention.

As shown in FIG. 1, the cell culture incubator of the present invention is comprised of a chamber 2 which is divided into an incubation portion 4 and a control portion 6 by wall 8. As best shown in FIGS. 2 through 6, chamber 2 is comprised of four modular components 10, 12, 14, and 16. Modular components 10, 12, 14, and 16 are preferably comprised of a synthetic polymer such as acrylic or the like and are preferably joined together by mating gaskets such that the bearing weight of modular components 10, 12, 14, and 16 joins them. As shown in FIG. 6, the joining of modular components 10, 12, 14, and 16 form chamber 2 of the cell culture incubator of the present invention in an economical and convenient manner.

Referring to FIGS. 1, 7, 8, and 9, chamber 2 of the cell culture incubator of the present invention includes four basic systems which optimally facilitate incubation of cell cultures: Temperature Regulation System, Media Circulation System, Gas Flow System, and Culture Agitation System.

Temperature Regulation System

The Temperature Regulation System includes air inlet 18 which allows air from the external environment to enter control portion 6 of chamber 2. Optimally, if improved sterility is desired, a filter 19 of, for example, 0.22 μm porosity can be placed adjacent air inlet 18 to ensure that ambient air entering control portion 6 of chamber 2 does not contain contaminants. Once air enters control portion 6 of chamber 2 through air inlet 18, it passes into hot box 20 through hot box inlets 22. Located within hot box 20 is a forced air heater 21 that increases the thermodynamic energy of the air in hot box 20. Heater 21, preferably mounted in wall 8, forces the heated air through wall 8, and then into incubation portion 4 where cell culture receptacle 28 (such as a HPBr hollow fiber device) is located. In order to maintain equilibrium, a portion of the now cooled air that was first heated and forced into incubation portion 4 from control portion 6 is recycled to hot box 20 in control portion 6 through conduits 23 that connect return openings 24 in hot box 20 to incubator portion air outlets 26 in wall 8. Heated air in incubation portion 4 that does not return to control portion 6 through incubation portion air outlet 26, is expelled into to the external environment through interstices between modular components 10, 12, 14, and 16. Thus, a substantially open, laminar flow system with minimal pressure build-up is provided. In this manner, rapid temperature responses combined with accurate and stable temperature control, relative to the set point, are achieved. Preferably, the slightly positive pressure in the incubation portion 4 of chamber 2 relative to ambient pressure reduces the possibility of contaminants from ambient air entering incubation portion 4 of chamber 2. In order to ensure the aforesaid accurate and stable temperature control, a temperature controller (FIG. 7) 29 such as Model No. CN76120 manufactured by Omega Engineering Incorporated of Stamford, Conn., which is a one-pulse output microprocessor with an alarm, may be employed. Additionally, located within incubation portion 4 of chamber 2 there is preferably located a thermocouple 30, for example, Model No. 5TC-TT-T-24-36 manufactured by Omega Engineering Incorporated of Stamford, Conn., which provides feedback to the above temperature controller 29 and is preferably insulated with, for example, "TEFLON" or the like.

In summary, the above temperature regulation system allows the desired thermodynamic energy to be provided for incubation portion 6 while maintaining a cooler environment in control portion 4 such that the electrical and mechanical components therein are not subject to thermodynamic-based fatigue and damage.

Culture Agitation System

Figure 10:
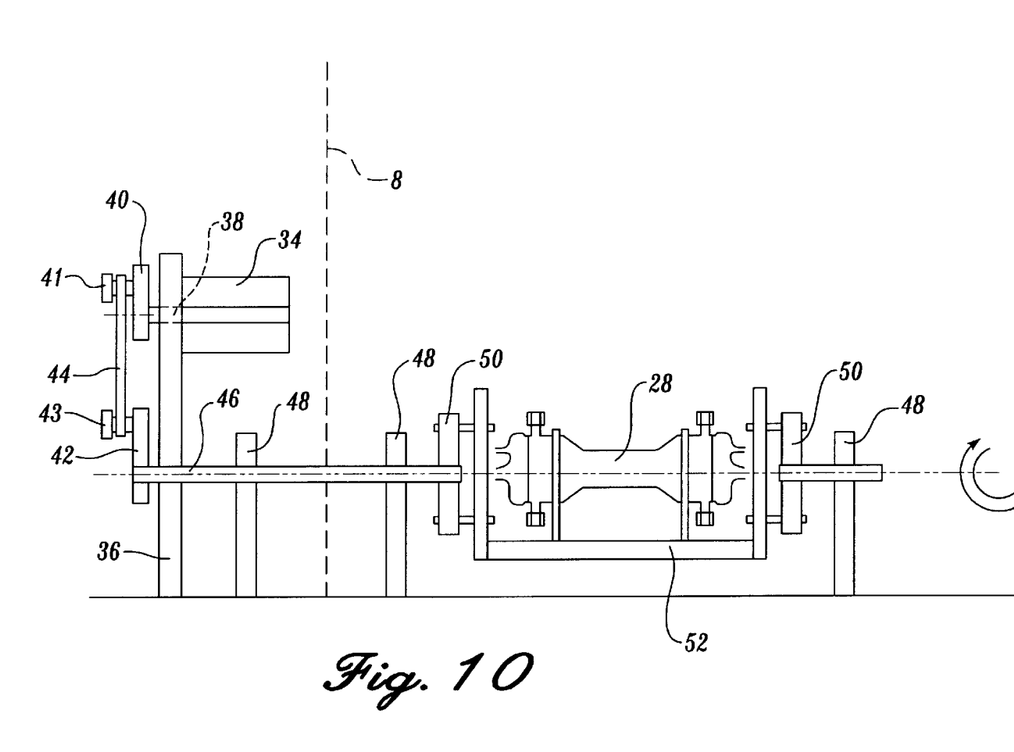
FIG. 10 is a detailed side view of the agitator assembly of the cell culture incubator of the present invention.
Figure 10A:
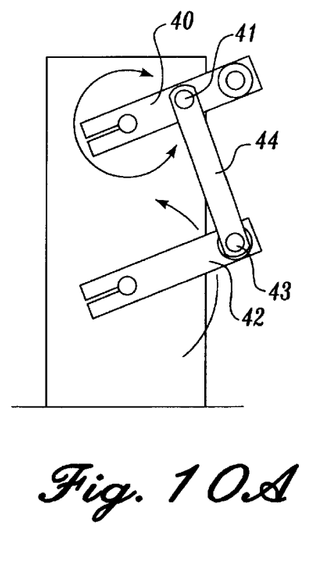
FIG. 10A is a detailed view of the crank, cam, and the rod of the agitator assembly of the cell culture incubator of the present invention.

The Culture Agitation System of the present invention, as best shown in FIGS. 1, 7, 9, 10, and 10A includes motor 34 located on motor mount 36 and having drive rod 38 passing through motor mount 36. Drive rod 38 is fixedly connected to crank 40, and crank 40 is connected to cam 42 by tie rod 44, as shown in FIG. 10A. It is to be noted that tie rod 44 is pivotally connected to both crank 40 and cam 42 at pivot points 41 and 43 that are offset from the axes of rotation of crank 40 and cam 42, respectively, such that 360 degree rotation of drive rod 38 and crank 40 causes a bi-directional partial rotation of about, for example, 120 degree of cam 42. Cam 42 is fixedly attached to axle 46, which is supported by axle mounts 48. It is important to note that all of the above elements are entirely located within the relatively cooler control portion 6 of chamber 2, with the exception of axle 46 which spans both control portion 6 of chamber 2 and incubation portion 4 of chamber 2, and some of axle mounts 48 which are located within incubation portion 4 of chamber 2. Also located within incubation portion 4 of chamber 2 are cradle supports 50 which connect cradle 52 to axle 46. In cradle 52 is located cell culture receptacle 28. In operation, the 360 degree rotation of drive rod 38 and crank 40, which is translated to approximately 120 degree bi-directional partial rotation of cam 42 and axle 46 by the interconnection of cam 42 and crank 40 by tie rod 44, causes approximately 120 degree bi-directional partial rotation of cradle 52 and cell culture receptacle 28 to effectuate the appropriate cell culture agitation within the cell culture receptacle 28. Motor 34 preferably has four settings; static, low (12±3 cpm), medium (30±3 cpm), and high (60±3 cpm).

While the above embodiment employs translation of 360 degree rotation to 120 degree bi-directional partial rotation, partial rotations of other degree components could be employed, as well as total 360 degree rotation, axial reciprocation, vertical reciprocation, or a combination of the above.

During cell culture agitation, it is often desirable to employ proactive media components in the cell culture. Preferably, chondroitin sulfate (Type C) is employed as a media component when anchorage dependent cells are cultured in order to enhance attachment to the carrier surface (e.g., microcarriers) during agitation. The preferred concentration range of chondroitin sulfate (Type C) is molecular weight dependent. However, at a mean molecular weight of about 4,000 daltons, the preferred concentration is in the range of about 0.005 mM to 0.5 mM.

Media Circulation System and Gas Flow System

Figure 11:
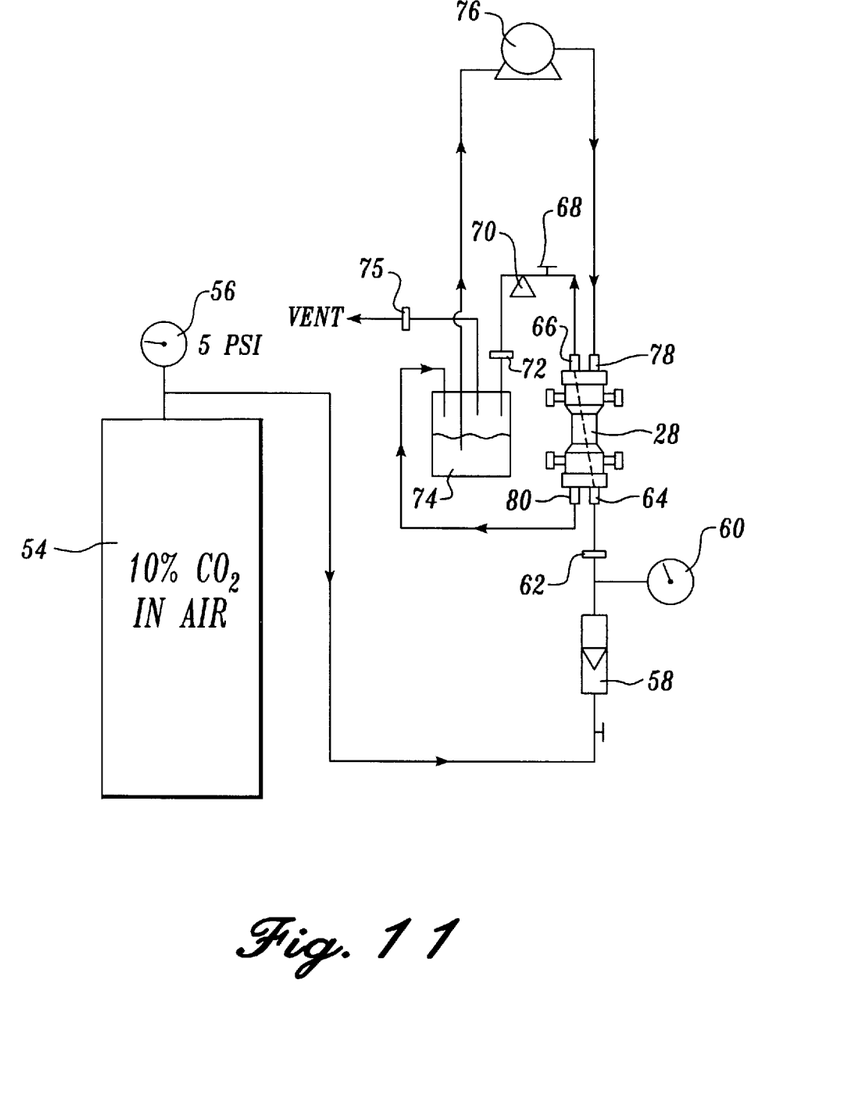
FIG. 11 is a schematic view of the nutrient and gas circulation system, continuous-batch process, for the cell culture incubator of the present invention.
Figure 12:
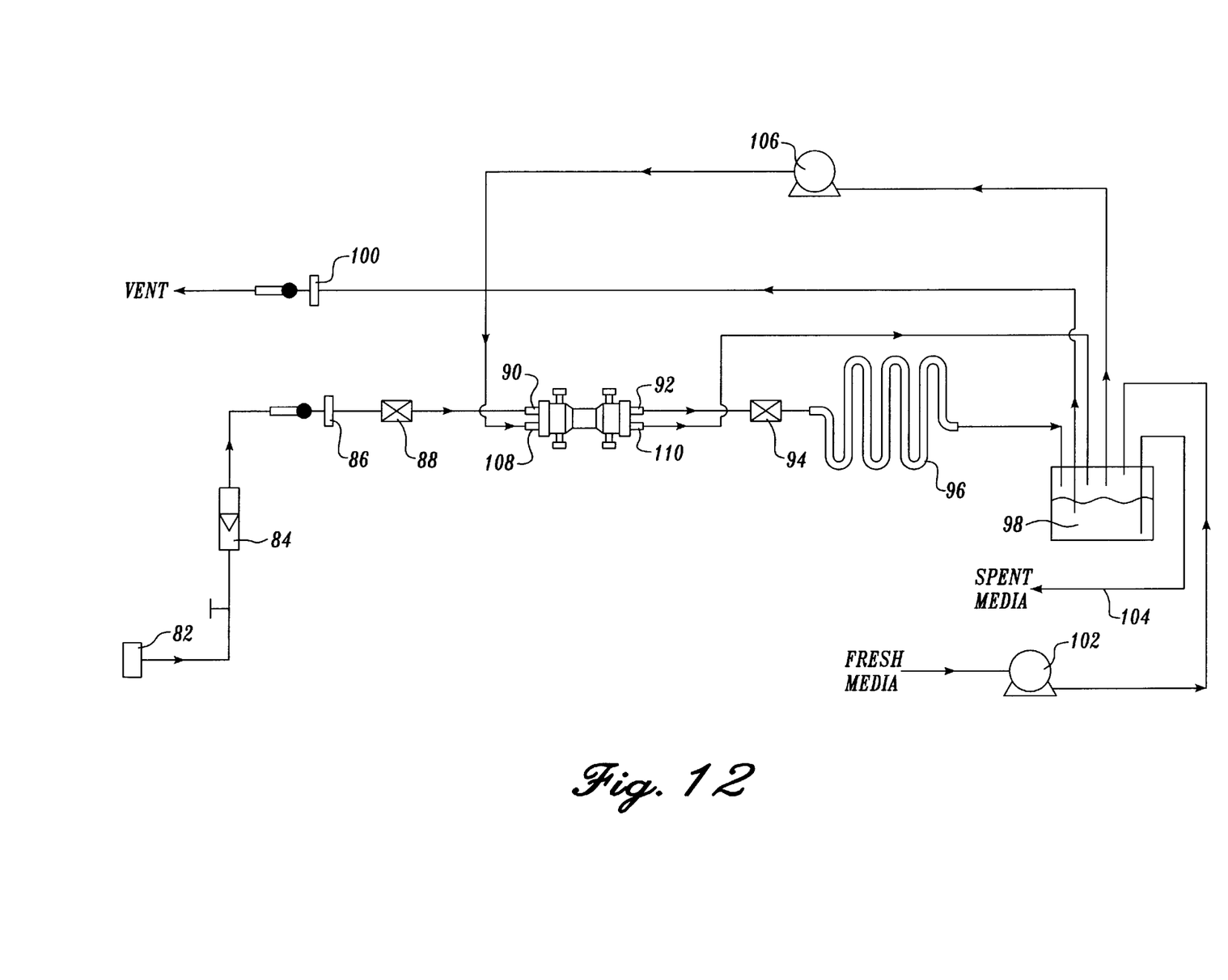
FIG. 12 is a schematic view of the nutrient and gas circulation system, continuous process, for the cell culture incubator of the present invention.
Figure 13:
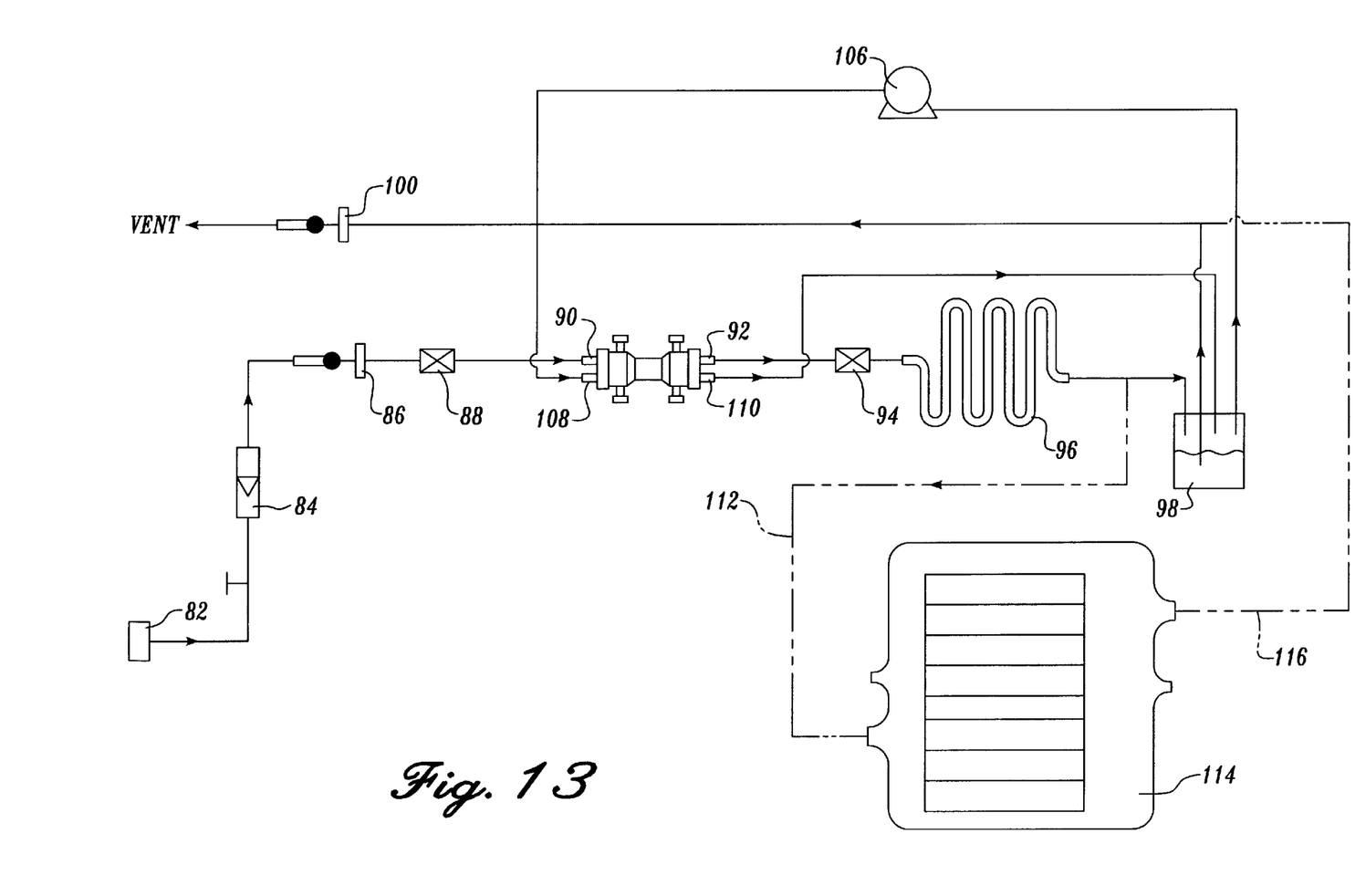
FIG. 13 is a schematic view of the nutrient and gas circulation system, auxiliary gas supply, for the cell culture incubator of the present invention.

The Media Circulation System and the Gas Flow System are two separate and discrete systems of the present invention, however they will be discussed in tandem for the sake of clarity with the divisions being based upon the type of process being employed or the presence of auxiliary functions as shown in FIGS. 11, 12, and 13. For example, FIG. 11 shows both the Media Circulation System and Gas Flow System used in a continuous-batch process, FIG. 12 shows the Media Circulation System and Gas Flow System in a continuous process and FIG. 13 shows the Media Circulation System and Gas Flow System employing an auxiliary gas supply.

First, referring to FIG. 11, which shows the Media Circulation System and Gas Flow System for the present invention employing a continuous-batch process, the Gas Flow System includes a gas source 54, for example about 10% $CO_2$ in air having a pressure valve 56 and supplying the pressurized gas at about 5 pounds per square inch, for example. Next, in the Gas Flow System, the pressurized gas passes through flow meter 58 which may be, for example, Model No. H-32013-01, a 50 milliliter per minute aluminum and stainless steel flow meter manufactured by Cole Parmer Instrument Company, Vernon Hills, Ill. An optional check valve and an optional flow restrictor (as shown in FIG. 12) set the back pressure of gas in cell culture receptacle 28 in conjunction with flow meter 58. When employed, the check valve is selected to prevent a maximum pressure of for example, about 0.5 to 1.0 psi. from being exceeded. Prior to entering cell culture receptacle 28, the gas passes through pressure gauge 60 to measure the back pressure in the cell culture receptacle 28, and then flows through hydrophobic filter 62, which is preferably a filter having a porosity of about 0.22 $\mu$m. After entering inlet 64 and infusing cell culture receptacle 28, the gas flows out of outlet 66 and through back pressure valve 68 and condenser 70. Condenser 70 is preferably a coiled section of the plastic tubing which preferably forms the lines of the Gas Flow System and the Media Circulation System. Most preferably, condenser 70 contains glass or plastic beads or particles to maximize the condensation of water vapor entrained by the gas in the cell culture receptacle 28. Next, the gas passes through another hydrophobic filter 72 having a preferred porosity of about 0.22 $\mu$m and then enters the head space of media reservoir 74; in this manner the preferably $CO_2$ containing gas maintains the required pH of the media. The gas is then expelled from the incubation portion 4 of chamber 2 through a gas vent orifice therein and into the external environment after passing through hydrophobic filter 75, preferably having a porosity of about 0.22 $\mu$m.

In the Media Circulation System of the continuous-batch process, media from media reservoir 74 passes through pump 76, which is preferably a peristaltic pump Model No. 15PB with a 200 cycle per minute motor manufactured by Barnat Company, Gilmont Instrument, Barrington, Ill. After passing through pump 76, the media enters inlet 78 of cell culture receptacle 28 where nutrients are provided to the culture. The spent media then passes through outlet 80 of cell culture receptacle 28 where it returns to media reservoir 74. Periodic changes of media reservoir 74 in a long-term cell culture procedure defines this process as a continuous-batch process Referring to FIG. 12, which shows the Media Circulation System and Gas Flow System for the present invention employing a continuous process, the gas flow system includes gas source 82 (for example, about 10% $CO_2$ in air at about 5 pounds per square inch), which communicates with flow meter 84 (for example, Model No. H-32013-01, a 50 milliliter per minute aluminum and stainless steel flow meter manufactured by Cole Parmer Instrument Company, Vernon Hills, Ill.). Hydrophobic filter 86, which preferably has a porosity of about 0.22 $\mu$m receives the gas from flow meter 84. Next, the gas flows through check valve 88 which, in conjunction with flow meter 84 and gas flow restrictor 94 (described later) sets the back pressure of gas in cell culture receptacle 28 to the predetermined level. Check valve 88 is selected to prevent a maximum pressure of, for example, about 0.5 to 1.0 psi from being exceeded. After entering inlet 90 and infusing cell culture receptacle 28, the gas flows out of outlet 92, through flow restrictor 94, and into condenser 96. Condenser 96 is preferably a coiled section of the plastic tubing, preferably made from the same material as the plastic tubing, which preferably forms the lines of the Gas Flow System and the Media Circulation System. Most preferably, condenser 96 contains glass or plastic beads or particles to maximize the condensation of water vapor entrained by the gas in the cell culture receptacle 28. The gas then flows into the head space of media reservoir 98; in this manner, the preferably $CO_2$—containing gas maintains the required pH of the media. The gas is then expelled from the incubation portion 4 of chamber 2 through a gas vent orifice therein and into the external environment after passing through hydrophobic filter 100, preferably having a porosity of about 0.22 $\mu$m.

In the Media Circulation System of the continuous process, fresh media is infused into media reservoir 98 from pump 106 while spent media from media reservoir 98 is discharged into the external environment through line 104. The amount of spent media passing through line 104 is directly proportional to the amount of fresh media being pumped into the closed system of media reservoir 98 by pump 106. Pump 102 is preferably a peristaltic pump Model No. 15PB with a 200 cycle per minute motor manufactured by Barnat Company, Gilmont Instrument, Barrington, Ill. Of like manufacture is pump 106 which takes up media from media reservoir 98 such that the media then enters inlet 108 of cell culture receptacle 28 where nutrients are provided to the culture. The spent media then passes through outlet 110 of cell culture receptacle 28 where it returns to media reservoir 98 to then pass through line 104 for discharge into the external environment.

Referring to FIG. 13, which shows the Media Circulation System and Gas Flow System for the present invention employing an auxiliary gas supply, like reference numbers used in FIG. 13 that are the same reference numbers used in FIG. 12 refer to the same elements as shown in FIG. 12. The embodiment of FIG. 13, in which an auxiliary gas supply is employed, differs from the continuous process embodiment in FIG. 12 in that pump 106, which supplies fresh media, and line 104, which discharges spent media to the external environment, and which are interconnected to media reservoir 98 in the continuous process embodiment of FIG. 12, are not present in the auxiliary gas supply embodiment of FIG. 13. Instead, in the auxiliary gas supply embodiment of FIG. 13, shunt 112 diverts a portion of the gas flow from condenser 96 that would enter media reservoir 98 and, instead, directs this portion of gas into flow through chamber 114, which is designed to contain static culture vessels such as culture plates, for example. After the gas has infused the cultures in flow through chamber 114, it exits chamber 114 through shunt 116 which joins the gas flow line from media reservoir 98 that ultimately vents to the external environment after first passing through hydrophobic filter 100.

Culture Examples

A sterile tubing set consisting of the Gas Flow System lines and Media Circulation System lines is assembled and integrated with the nutrient media reservoir 74, 98, employing standard sterile procedures in a biological hood. Alcohol swabs are placed over all fittings which will be connected to corresponding instrument fittings on the laboratory bench under ambient conditions. The entire assembly is transported to the cell culture incubator of the present invention. Alcohol swabs are employed to sterilize the instrument fittings before expeditiously removing the alcohol swabs from the tubing set fittings and completing the connections in a logical sequence.

Instrument settings (i.e., media circulation rate and gas flow rates) are selected and the tubing set leak tested for a period of time (e.g., 8–24 hours). To minimize cost, phosphate buffered saline (PBS) is recommended instead of media at this stage. However, this decision dictates that the instrument must be disassembled and the content of the media reservoir bottle changed before repeating the above steps and proceeding. Due to the relatively user friendly operational procedure, the cost savings will often more than justify the effort, with no significant risk of contamination. The gas source 54, 82 can be changed at any time. The recommended compositional range for most cell culture procedures is between 5–10% $CO_2$/air. The media circulation should be discontinued when gas flow is turned off to avoid flooding the oxygenator fibers in the cell culture receptacle 28, if an HPBr device. The present invention will maintain long-term culture with only periodic operator intervention (e.g., to take samples or to change spent media).

Both cells and microcarriers (for attachment of anchorage dependent cells) are introduced into the cell culture receptacle 28 by a hypodermic needle syringe. Similarly, cells and supernatant (i.e., used media) samples can be removed periodically from the cell culture receptacle 28 by displacement into an empty syringe with fresh media from a second syringe. While sampling with the door of the incubation portion 4 of chamber 2 open, the temperature controller 29 is switched off.

In order to periodically change spent media, the tubing set is disconnected and alcohol swabs placed over all fittings which have been disconnected. Under a biological hood, the media is exchanged and the long-term cell culture process resumed without delay.

EXAMPLE I

The invention employed an HPBr device as cell culture receptacle 28 and was assembled according to the configuration in FIG. 11. The cell culture receptacle 28 was inoculated with $3.5 \times 10^8$ viable 3C11 hybridoma cells and cultured for between 12–15 days in the following cell culture media: DMEM containing 4 mM L-glutamine, 1 mM glutamic acid, 2.5 mM benzoate buffer (comprised of equimolar ratio of benzoic acid and sodium benzoate), and 20% fetal bovine serum. Two liters of this media was used between day 1–7, which was replaced with fresh media on day 7. A pH of between about 7.0–7.4 was maintained through out the experiment (comprised of equimolar ratio of benzoic acid and sodium benzoate), and 20% fetal bovine serum. Two liters of this media was used between day 1–7, which was replaced with fresh media on day 7. A pH of between about 7.0–7.4 was maintained through out the experiment and media was recirculated at 100 mL/min. A 10% $CO_2$/air gas mixture was used at a flow rate of 63 mL(stp)/min and a back pressure of <1.0 psi was maintained for the duration of the experiment.

Four cell culture receptacles 28 were assemble in this manner, each using the following constant rotational speed through out the 12–15 day period: 1) static; 2) $12^{\pm}3$ cpm; 3) $30^{\pm}3$ cpm; and 4) $60^{\pm}3$ cpm. After allowing the cells to settle for 1 hour (every week day), 10 mL of supernatant was collected from the 17 mL volume within which the cells were cultured under perfusion conditions. The supernatant samples were stored at $-20°$ C. until they were required for $IgG_1$ monoclonal antibody concentration determination by an ELISA method. On completion of the 12–15 day culture period all the cells were recovered from the cell culture receptacle 28 (i.e. >95%) by expelling the cell/supernatant mixture with sterile air. Finally, the cell culture receptacle 28 was flushed twice with fresh media. The recovered cells were counted and viabilities were determined.

Figure 14:
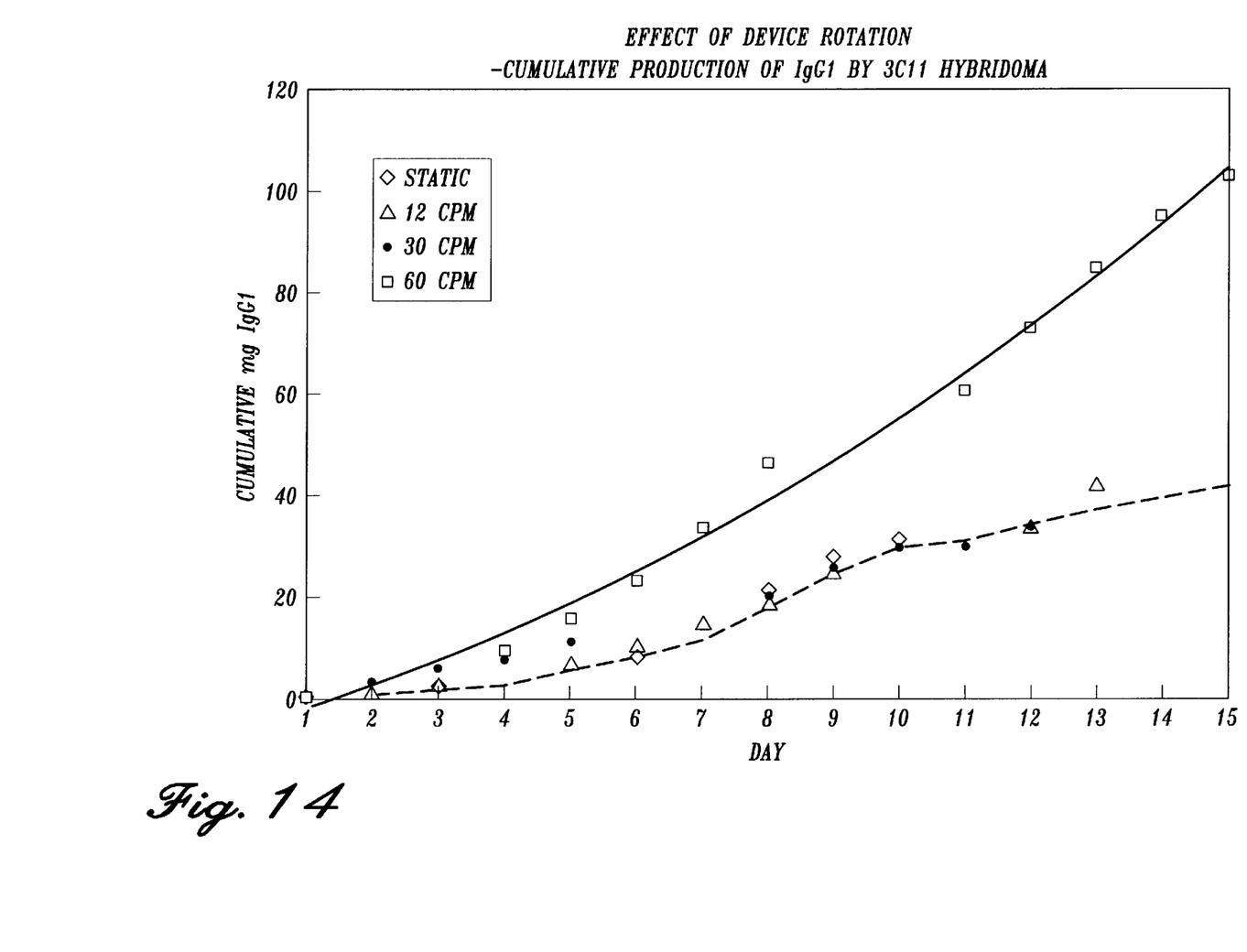
FIG. 14 is a graph of the effect of cell agitation in the cell culture incubator of the present invention on cumulative product of $IgG_1$ monoclonal antibody by 3C11 hybridoma cells.
Figure 15:
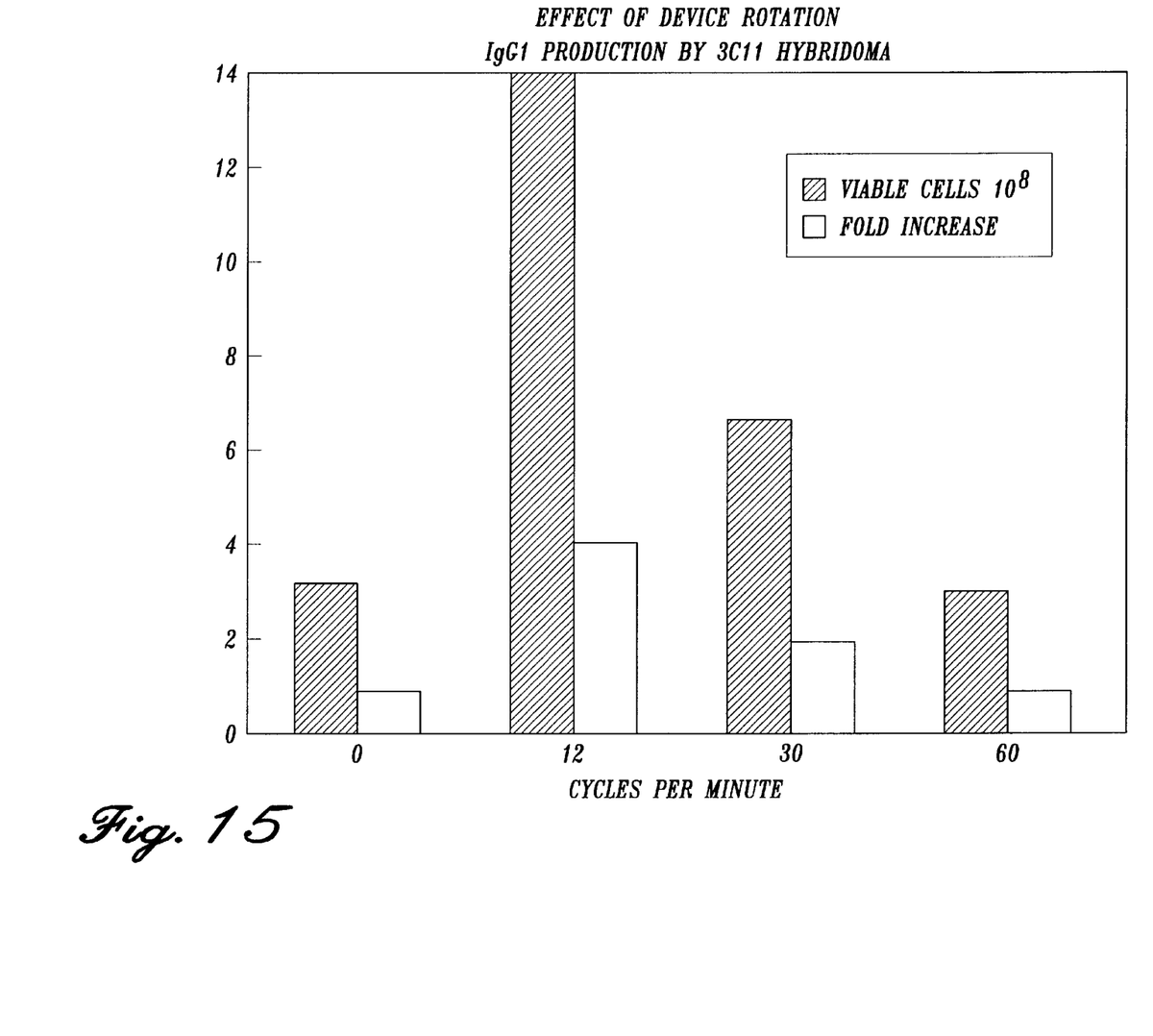
FIG. 15 is a bar graph of the effect of cell agitation in the cell culture incubator of the present invention on 3C11 hybridoma cell viability and fold increase.

FIGS. 14 and 15 demonstrate the effect of rotation speed on both antibody production and cell viability. It is evident that 60 cpm results in a dramatic increase in productivity (i.e. in the range of about 100%), with no net increase in viable cells during the course of the experiment. In the case of biomolecule production 60 cpm is preferred. Where the goal of a cell culture process is to expend and harvest viable cells, lower cpm values (i.e., 30 cpm, 12 cpm or even static) would be preferred.

EXAMPLE II

A series of four lipofection-based gene transfection experiments were conducted in the cell culture incubator of the present invention with an HPBr device being the cell culture receptacle. The control experiment was carried out in parallel with its own control which was done in multiwell plates in an incubator. The following experimental procedures were employed.

Plate Experiment

SW480 P3 (ATCC #CCL228) colon carcinoma cells were plated in 6-well (i.e., 1×106 viable cells per well). Thirteen wells were plated in this manner. Each well contained 3 mL of a stock solution comprised of 26.4 mL RPMI media, 4 mM L-glutamine 3.0 mL Fetal bovine serum, and 10 $\mu$g/mL gentamicin to make a total of 30 mL. Cells were cultured at 37° C. in a $CO_2$ incubator with 10% $CO_2$ for 24 hours prior to transfection. The cells were able to adhere to the plates during this period.

The transfection procedure was done by replacing the previous media in 1 mL OPTI-MEM media and adding a mixture of cationic lipid (DMRIE/DOPE) plasmid DNA (VR1412), both by Vical, Inc., San Diego, Calif. A molar ratio of 0.99 (i.e., 40 $\mu$L lipid: 10 $\mu$g DNA) diluted in 2.0 mL OPTI-MEM was applied to each well. These plates were incubated for 4 hours.

After 4 hours, heat deactivated fetal bovine serum plus 12.0 $\mu$L gentamicin were added to each well. For the following 13 days all of the cells from one well were trypsinized, counted, and 2×10$^4$ retained as a lysed sample for $\beta$-galactosidase reporter gene determination. The remaining wells were feed with 1 mL of the previously defined RPMI media every other day (starting 24 hours after transfection), without removing the DNA containing OPTI-MEM.

At the end of the 13 day period the lysate samples were assayed for $\beta$-galactosidase via a chlorophenol red-based procedure, which were quantitated with a UV-visible spectrophotometer.

HPBr Device Experiments

Four $\beta$-galatosidase reporter gene transfection experiments were conducted in four cell culture receptacles 28 that were HPBr-type devices with an equivalent protocol to that previously described to 6-well plates, except for the differences documented below. All features of the procedure were adjusted on a "per cell" basis. However, due to the perfusion mode of cell culture which is characteristic of the HPBr device (i.e., continuous feeding), there was no requirement for periodic feeding by hand.

Sufficient Cytodex 1 microcarriers (by Sigma, St. Louis, Mo.) were introduced into the side ports of the cell culture receptacle 28 after pre-swelling in phosphate buffered saline to have about 10 cells per microcarrier bead. 1×10$^7$ SW480 viable cells injected.

Table I lists the different media conditions for the first 24 hours after inoculation and post-transfection. It also identifies the rotation parameter employed in this study. 0.1 mM chondroitin sulfate (type C) was included in the OPTI-MEM transfection media for run Nos. 2, 3, and 4. While the recirculating OPTI-MEM media was replaced by transfection, the media in the compartment containing the cells was not.

Daily samples (about 1.5 mL) of cell/supernatant were taken from each cell culture receptacle 28 and an equal amount of fresh media was used to replace it. Cell count and viability was determined and 2×10$^7$ viable cells were lysed and retained for $\beta$-galactosidase determination.

TABLE I

| RUN TYPE | CONDITION | MEDIA COMPOSITION |
|---|---|---|
| 1. Plate | $CO_2$ Incubator [control] | 1 L RPMI (see above for composition) |
| 2. HPBr | 30 cpm | 839 mL RPMI; 10% fetal bovine serum; 4 mM L-glutamine; 10 g/mL gentamicin; 2.5 mM betizoate buffer; 0.1 mM chondroitin sulfate (also present in OPTI-MBM transfection media). |
| 3. HPBr | Static | Same as run #2. |
| 4. HPBr | 30 cpm for first 48 hr., then static | Same as run #2. |
| 5. HPBr | Static [control] | 1 L RPMI (see above for composition). |

Table II contains data comparing the four perfusion device experiments with the plate control. It is evident that an HPBr-type cell culture receptacle 28 operated in the cell culture incubator of the present invention can be employed to scale-up gene transfection and harvesting of cells, which may have therapeutic applications. This system can also be utilized as any artificial organ so that the long-term expression of the foreign gene can be easily and realistically studied; in a way equivalent to taking a biopsy from an intact organ in vivo. In this specific instance, the device is employed as a solid tumor model.

TABLE II

| Run | Experimental Conditions | TOTAL # CELLS (13 DAYS) | % VIABILITY | AREA UNDER CURVE (cm$^2$) | % INCREASED EXPRESSION PER 2 × 10$^4$ CELLS | ng/mL PER 2 × 10$^4$ CELLS AT DAY 13 | TOTAL EXPRESSION BASED ON VIABLE CELLS AT DAY 13 |
|---|---|---|---|---|---|---|---|
| 1 | Plate Control | 6.5 × 10$^6$ | 97% | 70 | — | 0.084 | 33 |
| 2 | 30 cpm | 1 × 10$^7$ | 86% | 84 | 20% | 0.120 | 65 |
| 3 | Static | 2.3 × 10$^7$ | 42% | 105 | 50% | 0.602 | 364 |
| 4 | 30 cpm/48 hr then static | 7.3 × 10$^7$ | 77% | 180 | 157% | 0.357 | 1254 |
| 5 | Bioreactor Control (Static) | 29.3 × 10$^7$ | 34% | 76 | 9% | 0.040 | 249 |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

What is claimed is:

1. A continuous cell culture incubator comprising:

a chamber divided into an enclosed incubation portion with air vent interstices and an enclosed control portion, said incubation portion in fluid communication with the control portion and maintained at a pressure sufficiently above surroundings to prevent ingress of contaminants;

a motor located in the control portion of said incubator;

a hollow fiber cell perfusion reactor in the incubation portion of said chamber, the reactor in mechanical communication with the motor, the motor urging bi-directional partial rotational motion of the reactor around a longitudinal axis of the reactor, when the motor is activated;

a temperature sensor in the incubator portion, the sensor in electrical communication with a source of heated air and a controller for the source of heated air, the source of heated air and the controller located in the control portion of the incubator, the control portion having an air inlet with a filter for filtering air entering said control portion and flowing to the source of heated air; and a nutrient circulation system and a gas circulation system each communicating with the cell perfusion reactor.

2. A cell culture incubator comprising:

a chamber divided into an incubation portion with air outlets and a control portion, said control portion having a heater wit a heated air outlet in communication with the incubator portion, the heater in electrical communication with a temperature sensor located in the incubation portion to heat filtered air from the external environment and transport the heated air to said incubation portion to maintain a predetermined temperature in said incubation portion, said incubation portion containing a hollow fiber cell perfusion bioreactor, the bioreactor in fluid communication with separate systems for supply of gas and nutrients, respectively, and the bioreactor linked to a motor, the motor imparting bi-directional partial rotation to the bioreactor about a longitudinal axis of the bioreactor to agitate contents thereof, when the motor is activated.

3. The incubator of claim 2 further comprising:

a wall dividing said chamber into said incubation portion and said control portion, said wall having openings therein for fluid communication between the portions;

a housing containing said heater and isolating said heater from the remainder of said control portion; and a conduit connecting said housing to one of said openings in said wall for recirculation of air from said incubation portion of said chamber back to said housing in said control portion of said chamber.

4. The incubator of claim 2, wherein said heater is a forced air heater that provides a positive pressure to said incubation portion of said chamber to reduce contamination in said incubation portion.

5. The incubator of claim 2, wherein said nutrient and gas supply systems comprise:

a gas source external to said incubation portion of said chamber; and tubing communicating said gas source with the bioreactor in said incubation portion of said chamber and with nutrient media.

6. The incubator of claim 5 further comprising:

a filter in an opening of said incubator portion of said chamber, said filter communicating with said tubing to remove contaminants from gas emanating from the perfusion bioreactor prior to venting to the external environment.

7. A temperature-controlled cell culture incubator comprising:

a chamber divided into an incubation portion and a control portion, said incubation portion containing a hollow fiber perfusion cell culture receptacle having a longitudinal axis;

a nutrient and gas circulation system communicating with the hollow fiber perfusion cell culture receptacle in said incubation portion of said chamber;

a controlled source of pressurizing heated air for maintaining a predetermined temperature in the incubation portion; and a motor mechanically communicating a bi-directional partial rotational movement around the longitudinal axis of the cell culture receptacle.

8. The incubator of claim 7, wherein said nutrient and gas circulation system comprises:

a gas source external to said incubation portion of said chamber; and tubing communicating said gas source with the hollow fiber perfusion cell culture receptacle in said incubation portion of said chamber, and with nutrient media.

9. The incubator of claim 8 further comprising:

a filter in an opening of said incubator portion of said chamber, said filter communicating with said tubing to remove contaminants from gas emanating from the cell culture receptacle prior to venting to the external environment.

10. The incubator of claim 7 further comprising:

a wall dividing said chamber into said incubation portion and said control portion, said wall having openings therein for fluid communication between the portions;

a housing in said control portion containing the controlled source of heated air, the housing separated from the remainder of said control portion; and a conduit connecting said housing to one of said openings in said wall for recirculation of air from said incubation portion of said chamber back to said housing in said control portion of said chamber.

11. The incubator of claim 7, wherein said source of heated air comprises a forced air heater that provides a positive pressure to said incubation portion of said chamber to reduce contamination in said incubation portion.

12. The incubator of claim 7 further comprising:

a filter between said control portion of said chamber and the external environment, said filter removing contaminants from the air provided to said control portion of said chamber to provide a sterile environment in said incubation portion.

* * * * *

UNITED STATES PATENT AND TRADEMARK OFFICE
CERTIFICATE OF CORRECTION

PATENT NO. : 5,882,918
DATED : March 16, 1999
INVENTOR(S) : R.A. Goffe

It is certified that error appears in the above-identified patent and that said Letters Patent is hereby corrected as shown below:

COLUMN  LINE

11         30         "wit" should read --with--
(Claim 2, line 4)

Signed and Sealed this

Twenty-eighth Day of March, 2000

*Attest:*

*Attesting Officer*

Q. TODD DICKINSON

*Commissioner of Patents and Trademarks*